US007217239B1

(12) United States Patent
Dyer

(10) Patent No.: US 7,217,239 B1
(45) Date of Patent: May 15, 2007

(54) SEMEN COLLECTION APPARATUS

(75) Inventor: Jack L. Dyer, Penrose, CO (US)

(73) Assignee: Reproduction Resources, Madison, WI (US)

( * ) Notice: Subject to any disclaimer, the term of this patent is extended or adjusted under 35 U.S.C. 154(b) by 468 days.

(21) Appl. No.: 10/839,009

(22) Filed: May 6, 2004

(51) Int. Cl.
*A61F 5/00* (2006.01)
*A61D 7/00* (2006.01)

(52) U.S. Cl. ........................................ 600/33; 600/38

(58) Field of Classification Search ............ 600/38–41, 600/33–35, 562, 573, 582; 604/317, 327, 604/328, 330, 331, 338–341, 345–347, 349–353; 128/830, 834, 835–844; 119/174, 854
See application file for complete search history.

(56) References Cited

U.S. PATENT DOCUMENTS 4,620,531 A * 11/1986 Dyer .......................... 604/349
4,744,352 A * 5/1988 Emery ........................ 604/349
5,695,446 A * 12/1997 Lindholm-Ventola ........ 600/38
6,520,922 B2 * 2/2003 Michelle ..................... 600/562

OTHER PUBLICATIONS

"Equimount" Phantoms, from http://web.archive,org/web/20010401165158/http://www.equimount.com/, 5 pages, Apr. 2001.*

"Equimount", from http://web.archive,org/web/20031212181625/http://www.equimount.com/, 4 pages, Dec. 2003.*

* cited by examiner

*Primary Examiner*—Samuel G. Gilbert
(74) *Attorney, Agent, or Firm*—G. F. Gallinger; Skinner and Associates

(57) ABSTRACT

An apparatus for collection of semen comprises: i) a frame forming an elongate body; ii) a base supporting the body; iii) a tubular receptacle containing an artificial vagina having a rear end portion pivotally carried on opposite lateral sides within the body, and an inner end portion releasably carried within the body, so that when the inner end portion is released collected semen therein will drain downwardly to an inner end portion; and, iv) a recessed rear access door, said door having an inner side portion positioned adjacent to the opening in the rear end portion of the tubular receptacle and an outer side portion positioned within an interior peripheral top and lateral side portions of the rear entry end of the body, so that downward and lateral components of thrust load exerted by the horse are largely sustained by the frame of the body, and wherein said recessed and protected door also has an enlarged thickness to accommodate a funnel shaped opening in the exterior side portion thereof to guide the horse into a central opening therein. When the horse is able to independently guide himself the apparatus is substantially more convenient and safer to use.

7 Claims, 1 Drawing Sheet

SEMEN COLLECTION APPARATUS

FIELD OF THE INVENTION

This invention relates to horse breeding and artificial insemination. More particularly this invention relates to an improved semen collection apparatus for collecting semen from a stallion.

BACKGROUND OF THE INVENTION

The best predictor and indication of the value of a horse is its bloodlines. A prize horse is largely valued for its potential for breeding. Breeding stallions are most in demand after they have had a long and distinguished show or racing career. Unfortunately these careers frequently over tax their joints and they have limited ability to breed. These mature animals are also more affected by disease and injuries which have affected their ability to stand or balance on their hind legs. Because transportation of horses is difficult, time consuming, and expensive, artificial insemination is widely practiced. The use of frozen collected semen for artificial insemination has only been widely accepted in the last five years. The breeding associations for quarter horses, (the largest registration of horses) as well as the breeding associations for appaloosa, and paint horses have only accepted the use of frozen semen in the last five years. And now, collected semen can be deposited by anyone, within a cooling container having a removable frozen pack, then couriered overnight for use the next day.

The most difficult aspect of artificial insemination has been collecting the semen from the horse. U.S. Pat. No. 4,620,531 was issued to Jack L. Dyer, the inventor herein, is for a semen collection apparatus. One of the problems with this apparatus was the rear entry door on the horizontal body. During use the door is subjected to continual downward pressure by the stallion's body as well as to forceful thrusting. Because of this downward pressure, and the lateral components of the thrusting, the door's thickness could not be excessive. Occasionally this door opened during use and the unpadded rear peripheral edge portion of the body injured the stallion. Another problem with this door was that it limited thickness minimized the potential to provide an interior funnel to guide a horse's penis to a central opening adjacent to the artificial vagina. It is significantly more convenient for the operator when all horses are able to guide themselves to the artificial vagina. It is critical for some horses, which refuse to continue, if they are handled to be guided to the artificial vagina. In addition to the safety of the horses another problem with this apparatus was the safety of the operator. With this apparatus the operator was too frequently required to get beneath the horse to initially guide the horse into the artificial vagina. And the operator was always required to get beneath the horses after semen was collected. Operators received frequent kicks from the flying front feet of the horse.

Another feature the original semen collection apparatus lacked was an ability to accommodate a stallion which had suffered back, and/or hind leg injuries, and/or any other neurological disorder which effects their ability to balance themselves while standing on only their hind legs. A surprising number of prize animals, due to a hock, stiffle, or back injuries sustained during a long show or racing career, are prevented from breeding due to an inability to wholly support and balance themselves standing wholly on their hind legs. Particularly West Nile virus, and equine protozoal myelitis (E.P.M.) which effect the horse's balance, have prevented many prize stallions from having a successful natural breeding career. Most horses are shown or raced at great expense primarily to pay off in a breeding career.

OBJECTS OF THE INVENTION

It is an object of this invention to disclose a more convenient semen collection apparatus. An apparatus which a horse is able to consistently and solely guide himself into without the assistance of an operator is much easier to use. It is yet a further object of this invention to disclose a safer semen collection apparatus. The apparatus disclosed herein requires infrequent operator positioning beneath the horse. The horse is also substantially safer. It is almost impossible for the horse to injure himself on the apparatus. It is a final object of this invention to disclose a semen collection apparatus which can accommodate a stallion which due to injury or illness is otherwise unable to breed.

One aspect of this invention provides for an apparatus for collection of semen comprising: i) a frame forming an elongate generally horizontal body having a rear entry end; ii) a base supporting and elevating the body; iii) a tubular receptacle containing an artificial vagina having a rear entry opening, a rear end portion, and an inner end portion, said rear end portion pivotally carried on opposite lateral sides within the body, and said inner end portion releasably carried within the body; so that when the inner end portion is released collected semen therein will drain downwardly to an inner end portion of the artificial vagina; and, iv) a recessed rear access door, said door having an inner side portion positioned adjacent to the opening in the rear end portion of the tubular receptacle and an outer side portion positioned within an interior peripheral top and lateral side portions of the rear entry end of the body, so that downward and lateral components of thrust load exerted by the horse are largely sustained not by the door, but by the frame of the body, and wherein said recessed and protected door also has an enlarged thickness to accommodate a funnel shaped opening in the exterior side portion thereof so that the horse is guided and funnelled into a central opening in the door. When the horse is able to independently guide himself into the artificial vagina the apparatus is substantially more convenient and safer to use.

In a preferred aspect of this apparatus the inner end portion of the tubular receptacle may be released remotely so that the operator need not endanger himself by positioning himself beneath the horse.

In yet another aspect of this invention the base comprises a column, and the body is hinged to the column, so that a rear end of the body may be lowered with respect to the front end portion of the body to accommodate a stallion injured, ill, or otherwise unable to stand and balance on his hind legs for breeding.

Various other objects, advantages and features of this invention will become apparent to those skilled in the art from the following description in conjunction with the accompanying drawings.

FIGURES OF THE INVENTION

Figure 1:
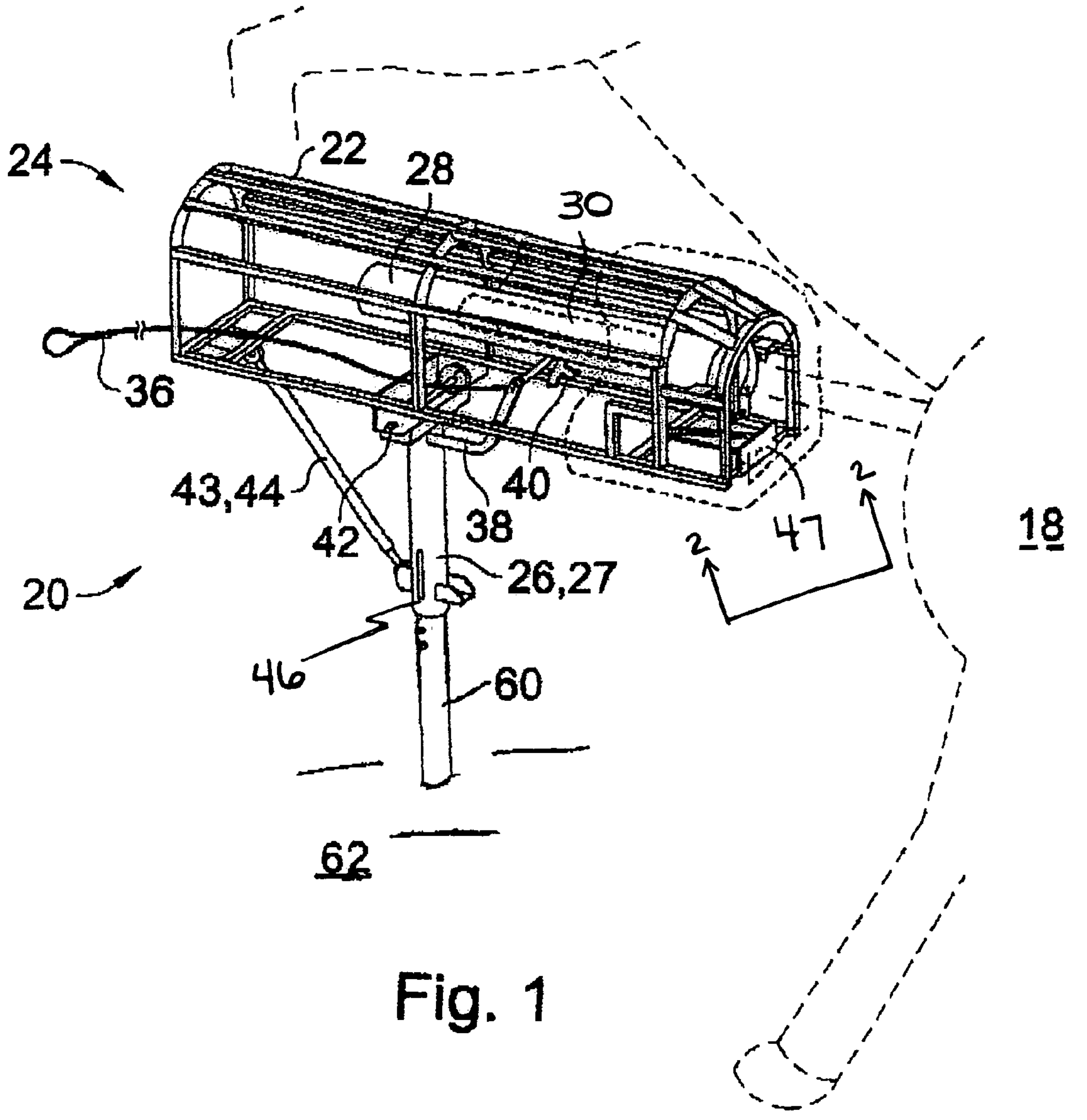
FIG. 1 is a perspective view of a semen collection apparatus having an improved rear entry door and a positioning mechanism to accommodate an injured horse.

The following is a discussion and description of the preferred specific embodiments of this invention, such being made with reference to the drawings, wherein the same reference numerals are used to indicate the same or similar parts and/or structure. It should be noted that such discussion and description is not meant to unduly limit the scope of the invention.

DESCRIPTION OF THE INVENTION

Turning now to the drawings and more particularly to FIG. 1 we have a perspective view of a semen collection apparatus 20 having an improved rear entry door 32 and a positioning mechanism 43 to accommodate an injured horse 18. The apparatus 20 for collection of semen comprises: i) a frame 22 forming an elongate generally horizontal body 24 having a rear entry end; ii) a base 26 supporting and elevating the body 24; iii) a tubular receptacle 28 containing an artificial vagina 30 and having a rear entry opening, a rear end portion, and an inner end portion, said rear end portion pivotally 32 carried on opposite lateral sides within the body 24, and said inner end portion releasably carried within the body 24. When the inner end portion is released collected semen therein will drain downwardly to an inner end portion of the artificial vagina 30.

Figure 2:
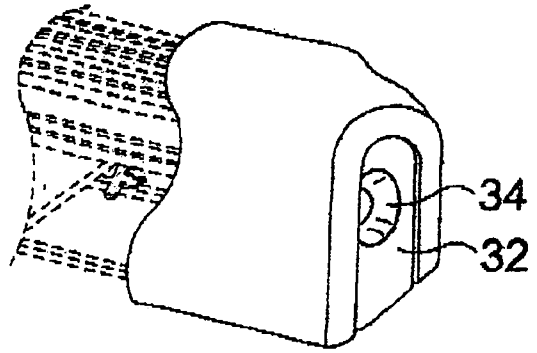
FIG. 2 is an enlarged perspective view of the rear entry door as viewed along line 2—2 on FIG. 1.

FIG. 2 is an enlarged perspective view of the rear entry door as viewed along line 2—2 on FIG. 1. iv) A recessed rear access door 32 has an inner side portion positioned adjacent to the opening in the rear end portion of the tubular receptacle 28 and an outer side portion positioned within an interior peripheral top and lateral side portions of the rear entry end of the body 24. Downward and lateral components of thrust load exerted by the horse 18 are largely sustained not by the door 32, but by the frame 22 of the body 24 because said door 32 is recessed and accordingly protected therefrom. Because the door 32 is protected, the door 32 can have an enlarged thickness to accommodate a funnel shaped opening 34 in the exterior side portion thereof.

The horse then is much better guided and funnelled into a central opening in the door 32. When the horse is able to independently guide himself, without manual assistance this makes the apparatus 20 much more convenient to use. It also makes the apparatus 20 much safer to use. It eliminates the necessity of the operator positioning himself beneath the horse 18. It also enables some horses to be bred which refuse to proceed when they are handled.

In the most preferred aspect of this invention a hinge 47 attaches a bottom side portion of the door 32 to the frame 22 of the body 24. Top and lateral peripheral side portions of the body 24 extend further rearwardly than the bottom side portion of the frame 22 to facilitate opening of the door 32. The bottom portion of the frame 22 which does not extend as far rearwardly as the top and lateral side portions of the frame 22 protects the testicles of the horse from being crushed by the body 24.

If the inner end portion of the tubular receptacle 28 is released remotely then the operator need not endanger himself by positioning himself beneath the horse. In the most preferred aspect of this invention a cord 36, and an arm 38 and a stop 40 are provided. Said arm 38 has a lower end portion pivoted to the frame 22, and a top end portion carrying the tubular receptacle 28. Said top end portion of the arm 38 has one end of the cord 36 attached thereto. Said stop 40 holds the arm 38 in an upright position just beyond a vertical position. When the other end of the cord 36 is pulled forwardly, the arm 38 is pulled off the stop 40 and the inner end portion of the tubular receptacle 28 is released thereby causing the tubular receptacle 28 to tilt and collected semen therein to drain toward an inner end of the artificial vagina 30.

In a preferred aspect of this invention the base 26 comprises a column 27, and wherein the body 24 is hinged 42 to the column 27 so that a rear end of the body 24 may be lowered with respect to the front end portion of the body 24 to accommodate a horse 18 unable to stand and balance on his hind legs for breeding. When the rear portion of the body is tipped down with the front portion elevated the front portion of the horse's weight is still supported. Simply lowering the entire body 24 of the apparatus 20 will not allow the horse 18 to balance, and will not work. In the most preferred aspect of this invention the positioning mechanism 43 comprises a turn buckle 44 is used to tip the body 24 on the hinge 42. Most preferably the body 24 further comprises a substantial height adjustment 46 on the base 26 to facilitate lowering the front end portion of the body 24 when the rear end portion is tipped and lowered down. It is common for a stallion to be most highly valued for breeding after a long and distinguished career of many shows. And it is not uncommon for such a stallion to have sustained knee and ankle injuries in such a career preventing that stallion from standing wholly on his hind legs. The innovation disclosed herein facilitates breeding such an injured stallion.

As was disclosed in U.S. Pat. No. 4,620,531, which is incorporated here into by reference, the body frame 22 is covered first in expanded metal, and then by foam, and finally by vinyl. It is further noted that while the column 27 of the base 26 may be positioned within an embedded tube (not shown), it has been generally found that it is more convenient to support the base 26 on legs 60 in ground 62.

While the invention has been described with preferred specific embodiments thereof, it will be understood that this description is intended to illustrate and not to limit the scope of the invention, which is defined by the following claims.

I claim:

1. An apparatus for collection of semen comprising:

i) a frame forming an elongate generally horizontal body having a rear entry end;

ii) a base supporting and elevating the body;

iii) a tubular receptacle containing an artificial vagina having a rear entry opening, a rear end portion, and an inner end portion, said rear end portion pivotally carried on opposite lateral sides within the body, and said inner end portion releasably carried within the body; so that when the inner end portion is released collected semen therein will drain downwardly to an inner end portion of the artificial vagina; and, iv) a recessed rear access door, said door having an inner side portion positioned adjacent to the opening in the rear end portion of the tubular receptacle and an outer side portion positioned within an interior peripheral top and lateral side portions of the rear entry end of the body, so that downward and lateral components of thrust load exerted by the horse are largely sustained not by the door, but by the frame of the body, and wherein said door also has an enlarged thickness accommodating a funnel shaped opening in the exterior side portion thereof so that the horse's penis is guided and funnelled into a central opening in the door.

2. An apparatus as in claim 1 further comprising a hinge attaching a bottom side portion of the door to the frame of the body, and wherein said top and lateral peripheral side portions of the body extend further rearwardly than the bottom side portion of the frame to facilitate opening of the door and protect the testicles of the horse from being crushed by the body.

3. An apparatus as in claim 2 wherein the inner end portion of the tubular receptacle may be released remotely so that the operator need not endanger himself by positioning himself beneath the horse.

4. An apparatus as in claim 3 further comprising a cord, and an arm and a stop, said arm having a lower portion pivoted to the frame and a top end portion carrying the inner end portion of the tubular receptacle, said top end portion of the arm having one end of the cord attached thereto; and said stop holding the arm in an upright position just beyond a vertical position; so that when the other end of the cord is pulled forwardly, the arm is pulled off the stop and the inner end portion of the tubular receptacle is released thereby causing the tubular receptacle to tilt and collected semen therein to drain toward an inner end of the artificial vagina.

5. An apparatus as in claim 1 wherein the rear end of the body is lower than a front end portion of the body to accommodate a stallion injured, ill, or otherwise unable to stand and balance on his hind legs for breeding.

6. An apparatus as in claim 5 wherein the base comprises a column, and wherein the body is hinged to the column, so that a rear end of the body may be lowered with respect to the front end portion of the body to accommodate a stallion injured, ill, or otherwise unable to stand and balance on his hind legs for breeding.

7. An apparatus as in claim 6 further comprising a turn buckle to tip the body on the hinge; and further comprising a substantial height adjustment on the base to facilitate lowering the front end portion of the body when the rear end portion is lowered.

* * * * *